United States Patent [19]
Soldati et al.

[11] 4,184,039
[45] Jan. 15, 1980

[54] BENZOTHIADIAZINE 1, 1-DIOXIDES

[76] Inventors: Gianluigi Soldati, 486 Flock Rd., Mercerville, N.J. 08619; David A. Schlichting, Rolling Meadow Ln., Pound Ridge, N.Y. 10576; Paul Finkelstein, 10 Springwood Dr., Princeton Junction, N.J. 08550

[21] Appl. No.: 856,497

[22] Filed: Dec. 1, 1977

[51] Int. Cl.² ............................................. C07D 285/22
[52] U.S. Cl. ...................................... 544/12; 424/246
[58] Field of Search ........................................... 544/12

[56] References Cited

U.S. PATENT DOCUMENTS

| | | | |
|---|---|---|---|
| 3,043,840 | 7/1962 | Downing | 544/12 |
| 3,251,837 | 5/1966 | Holland | 544/12 |
| 3,290,302 | 12/1966 | Eloy | 544/12 |
| 3,345,365 | 10/1967 | Topliss et al. | 544/12 |
| 3,361,816 | 1/1968 | Topliss et al. | 544/12 |

*Primary Examiner*—Ethel G. Love
*Attorney, Agent, or Firm*—Kevin B. Clarke

[57] ABSTRACT

Novel Benzothiadiazines which stimulate hair growth when applied intraperitoneally, orally or topically.

2 Claims, No Drawings

BENZOTHIADIAZINE 1,1-DIOXIDES

Benzothiadiazine dioxides are known chemical entities with antihypertensive and antihypoglycemic activity. It has previously been reported that patients when treated for a prolonged period of time with diazoxide administered orally developed uncontrolled hair growth on the forehead, dorsal surfaces of the trunk and arms, thigh, calf and face.

It has now been found that the novel benzothiadiazines of the present invention, in addition to their antihypertensive and antihypoglycemic properties, promote hair growth which is confined to the area of application.

This invention relates to novel benzothiadiazines, namely 1, 2, 4-benzothiadiazine 1,1-dioxides (I) and 3,4-dihydro-1,2,4-benzothiadiazine 1,1-dioxides (II), both substituted at the benzene ring in 6 or 8 position and in 3 position. These new compositions are represented by the general formulas:

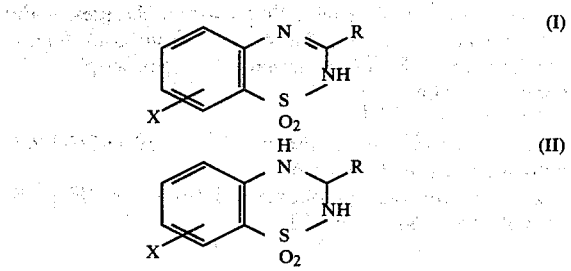

More specifically when X represents a chlorine in the 6 position, R is 2,4,4-trimethylpentyl, octyl, or dimethylaminoethoxymethyl in compounds of type I, or cyclohexenyl in compounds of type II.

When X is a chlorine in the 8 position, R is heptyl in type I and styryl in type II.

Also, for compounds of general formula I when X is 6-methyl R is propyl, and when X is a 6-methoxy R is ethyl.

We have found that these new benzothiadiazines facilitate hair growth, and such growth can be achieved by topical application, as well as by other routes, and that hair growth is confined to the area of application, such as the scalp when applied topically in suspension or in solution. Moreover these new compositions when applied, even at low concentration, to test animals, cause a growth of new hair, this growth being of cosmetic significance.

Several species of hairless mice and rhinocerous mice were studied for this response. Only one hairless mouse species responded well. Screening experiments were done in these mice. These experiments consisted of daily i.p. injections of the chemicals in solution (DMSO) or suspension in doses of up to 100 mg/kg/day for two months during which time hair growth could be observed visually. Hairless mice responded to treatment by growing hair in several areas of the back. At the end of the experiment the animals were sacrificed, histological slides of various skin areas were prepared and examined microscopically. The number of hairs in various stages of growth were quantitatively determined (trichogram) and evaluated statistically.

Selected compounds were studied in balding monkeys orally, intraperitoneally and topically and found to be active. Both suspensions and solutions were studied. Surprisingly the suspensions were found to be most active. Visual and histological growth was noted. We also found that these compounds when applied topically, retarded the loss of hair in monkeys.

The following experimental drug dosage forms, and dose routes of administration were used in monkeys: solution in DMSO at 20 to 100 mg/kg/day intraperitoneally, a suspension in fruit juice at up to 100 mg/kg/day orally, a solution in DMSO at up to 10 mg/kg/day topically and a suspension up to 10 mg/kg/day topically.

Observations of treated and untreated animals were made at biweekly intervals for 8 weeks.

The following compounds were prepared. All were identified by I.R. Spectroscopy, elemental analysis or by N.M.R.

COMPOSITIONS OF TYPE I

1. X=6-chloro, R=2,4,4-trimethylpentyl; Mp. 243°–4°; Calculated for $C_{15}H_{21}ClN_2O_2$: C% 54.79, H% 6.44; N% 8.52. Found: C% 55.08; H% 6.64; N% 8.46.

2. X=6-chloro, R=octyl; Mp. 234°–6°; Calculated for $C_{15}H_{21}ClN_2O_2S$: C% 54.79; H% 6.44; N% 8.52. Found: C% 55.15%; H% 6.50; N% 8.31.

3. X=8-chloro, R=heptyl; Mp. 168°–70°. NMR in acetone-$d_6$ shows peaks at 0.9–1; 1.2–1.6; 1.6–2.0; 2.4–2.8; 7.2–7.5; 7.6,7.7 ppm. Calculated for $C_{14}H_{19}ClN_2O_2S$: C% 53.41; H% 6.08; N% 8.89. Found: C% 53.71; H% 6.17; N% 9.08.

4. X=6-chloro, R=dimethylaminoethoxymethyl; Mp 219°–221°, NMR of the hydrochloride salt shows peaks at 3.5, 3.8–4.0, 4.2–4.4, 4.75, 7.3, 7.5 and 7.6–7.9 ppm in $D_2O$-DDS. Calculated for $C_{12}H_{16}ClN_3O_3S$: C% 45.35; H% 5.07; N% 13.22. Found: C% 45.48; H% 5.30; N% 13.49.

5. X=6-methoxy; R=ethyl; Mp.205°–7°. calculated for $C_{10}H_{12}N_2O_3S$: C% 49.82; H% 5.35. Found: C% 50.00; H% 5.24.

6. X=6-methyl, R=propyl; Mp. 204°–6°; calculated for $C_{11}H_{14}N_2O_2S$: C% 55.45; H% 5.92; N% 11.76. Found: C% 55.36; H% 5.96; N% 11.98.

COMPOSITION OF TYPE II

7. X=chloro, R=cyclohexenyl; Mp.252°–4°; calculated for $C_{13}H_{15}ClN_2O_2S$: C% 52.26; H% 5.06; Found: C% 52.39; H% 5.00. NMR shows peaks at 1.9–2.4, 3, 4.6–5, 5.7–5.8, 6–6.6,6.7–6.8, 6.8–6.9, 6.9–7.1, 7.5, 7.65 ppm.

8. X=8-chloro, R=styryl; Mp.225°–7°; calculated for $C_{15}H_{13}ClN_2O_2S$: C% 56.17; H% 4.08; N% 8.73. Found: C% 56.03; H% 4.03; N% 8.59.

Methods of preparation of benzothiadiazines are reported in the literature (J. G. Topliss, et al., U.S. Pat. No. 2,986,573 (1961), J. Med. Chem. 6, 122–127 (1963); J. Med. Chem. 7, 269–273 (1964); B. A. Bierbaum et al., J. Med. Chem.6, 272–275 (1963).

The following examples are given by way of illustration of the methods of preparing the compounds of the present invention:

EXAMPLE I

6-CHLORO-3-CYCLOHEXENYL-3,4-DIHYDRO-2H-1,2,4-BENZOTHIADIAZINE 1, 1-DIOXIDE.

4-chloro-2-aminobenzenesulfonamide (20 g.) and 12 g. of 3-cyclohexene carboxaldehyde are combined in 150 ml. of acetonitrile and refluxed 4½ hours. The precipitate which forms during refluxing and on cooling is collected by filtration and washed with cold acetonitrile. The crude (17.4 g) is recrystallized from dimethylformamide-water to give a white product melting at 252°–4°. Analysis calculated for $C_{13}H_{15}ClN_2O_2S$: C% 52.26, H% 5.06. Found: C% 52.39; H% 5.00.

EXAMPLE II

6-CHLORO-3DIMETHYLAMINOETHOXYMETHYL-2H-1,2,4-BENZOTHIADIAZINE 1,1-DIOXIDE.

16 g. of 6-chloro-3-chloromethyl-2H-1,2,4-benzothiadiazine, 1,1-dioxide and 25 g. of dimethylaminoethanol are dissolved in 110 ml. of acetone and refluxed 45 minutes. The solvent is then removed under reduced pressure and the residue heated for 1-½ hours at 120°–140°, oil bath temperature. After cooling the solid material is collected and recrystallized from ethanol. Mp. 219°–221°, Yield 6.5 g. The hydrochloride was made (mp over 300) and the structure identified by N.M.R. in D$_2$O-DDS. This shows the methyl groups at 3.5 ppm, the methylene groups at 3.5, 3.8–4, 4.2–4.4 and 4.75 ppm. The protons on the benzene ring show at 7.3, 7.5 and 7.6–7.8 ppm.

EXAMPLE III

6-CHLORO-3-(2,4,4-TRIMETHYLPENTYL)-2H-1,2,4-BENZOTHIADIAZINE 1,1-DIOXIDE.

Isononyl chloride (20 g) dissolved in 50 ml toluene is added dropwise to a hot and stirred solution of 20 g. of 2-aminobenzenesulfonamide in 400 ml benzene and 150 ml toluene. At the end of the addition stirring and heating is continued for 5 hrs. The solution is filtered and part of the solvent is evaporated. Hexane is added and the precipitate is collected and dried. 20 g. of this crude product are combined with 400 ml of 10% aqueous sodium hydroxide and heated for 2 hrs. The alkaline solution is then cooled and slowly acidified with hydrochloric acid. The solid formed is collected and washed several times with water. Yield 17.8 g. Recrystallized twice from methanol, m.p. 243°–4°. Analysis calculated for $C_{15}H_{21}ClN_2O_2S$: C% 54.79, H% 6.44, N% 8.52. Found: C% 55.08, H% 6.64, N% 8.46.

It is to be understood that the form of this invention herein shown and described is to taken as the preferred examples of the same, and that various changes in the operable conditions may be resorted to without departing from the spirit of the invention or the scope of the subjoined claims.

We claim:
1. 6-chloro-3-dimethylaminoethoxymethyl-2H-1,2,4-benzothiadiazine 1,1-dioxide.
2. 6-chloro-3-cyclohexenyl-3,4-dihydro-2H-1,2,4-benzothiadiazine 1,1-dioxide.

* * * * *